United States Patent [19]
Klutchko et al.

[11] 3,937,837
[45] Feb. 10, 1976

[54] SUBSTITUTED CHROMONE-3-CARBONITRILES, CARBOXAMIDES AND CARBOXYLIC ACIDS USEFUL FOR PREVENTING ASTHMATIC SYMPTOMS

[75] Inventors: Sylvester Klutchko, Hackettstown; Richard E. Brown, Hanover; Maximilian Von Strandtmann, Rockaway, all of N.J.

[73] Assignee: Warner-Lambert Company, Morris Plains, N.J.

[22] Filed: Sept. 9, 1974

[21] Appl. No.: 504,628

Related U.S. Application Data

[62] Division of Ser. No. 312,154, Dec. 4, 1972, Pat. No. 3,862,143.

[52] U.S. Cl. ............................................. 424/283
[51] Int. Cl.² ....................................... A61K 31/35
[58] Field of Search .................. 424/283; 260/345.2

[56] References Cited
UNITED STATES PATENTS 3,692,796   9/1972   Freedman ...................... 260/345.2

*Primary Examiner*—Frederick E. Waddell
*Assistant Examiner*—Allen J. Robinson
*Attorney, Agent, or Firm*—Albert H. Graddis; Frank S. Chow; Anne M. Kelly

[57] ABSTRACT

Substituted chromone-3-carbonitriles, carboxamides and carboxylic acids having the structural formula:

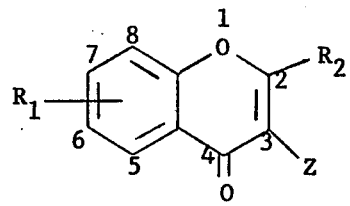

wherein $R_1$ represents hydrogen, halogen, lower alkyl, hydroxy, lower alkoxy, or acyloxy; $R_2$ represents hydrogen, lower alkyl, fluorinated lower alkyl, alkoxycarbonyl, carboxy, or lower alkyl carboxylic acid; Z represents cyano, carboxy, alkoxycarbonyl, or

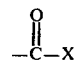

wherein X represents amino, N-lower-alkylamino, hydroxylamino, N-lower-alkylhydroxylamino, ureido, piperidino, or anilino, with the proviso that when $R_2$ represents hydrogen, Z represents cyano or

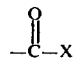

wherein X has the same meaning as given above; and wherein $R_2$ and Z together may form a substituted pyrrole ring; and the corresponding non-toxic, pharmaceutically acceptable salts.

1 Claim, No Drawings

SUBSTITUTED CHROMONE-3-CARBONITRILES, CARBOXAMIDES AND CARBOXYLIC ACIDS USEFUL FOR PREVENTING ASTHMATIC SYMPTOMS

This is a division of application Ser. No. 312,154 filed Dec. 4, 1972, now U.S. Pat. No. 3,862,143.

The present invention relates to substituted chromone-3-carbonitriles, carboxamides and carboxylic acids having the following structural formula:

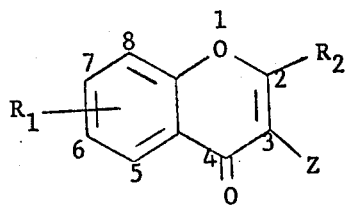

I wherein $R_1$ represents hydrogen, halogen, lower alkyl, hydroxy, lower alkoxy, or acyloxy; $R_2$ represents hydrogen, lower alkyl, fluorinated lower alkyl, alkoxycarbonyl, carboxy, or lower alkyl carboxylic acid; Z represents cyano, carboxy, alkoxycarbonyl, or

wherein X represents amino, N-lower-alkylamino, hydroxylamino, N-lower-alkylhydroxylamino, ureido, piperidino, or anilino, with the proviso that when $R_2$ represents hydrogen, Z represents cyano or

wherein X has the same meaning as given above; and wherein $R_2$ and Z together may form a substituted pyrrole ring; and the corresponding non-toxic, pharmaceutically acceptable salts.

Among the preferred species of substituted chromone-3-carbonitriles, carboxamides and carboxylic acids, there may be mentioned those compounds having structural formula I above wherein $R_1$ represents hydrogen, halogen, lower alkoxy, hydroxy or acetoxy; $R_2$ represents hydrogen, lower alkyl, trifluoromethyl, alkoxycarbonyl, carboxy or lower alkyl carboxylic acid; Z represents cyano, carboxy, alkoxycarbonyl or

wherein X represents amino, N-lower-alkylamino, hydroxylamino, N-methylhydroxylamino, ureido, piperidino, or anilino, with the proviso that when $R_2$ represents hydrogen, Z represents cyano, or

wherein X has the same meaning as given above; and wherein $R_2$ and Z together may form a dioxo-substituted pyrrole ring; and the corresponding non-toxic, pharmaceutically acceptable salts thereof.

A particularly preferred group of compounds having structural formula I above are those wherein $R_1$ represents hydrogen, halogen, lower alkoxy, hydroxy or acetoxy; $R_2$ represents hydrogen, lower alkyl, trifluoromethyl, alkoxycarbonyl, carboxy, or lower alkyl carboxylic acid; and Z represents cyano, or

wherein X represents amino, N-lower-alkylamino, hydroxylamino, N-methylhydroxylamino, ureido, piperidino, or anilino; and wherein $R_2$ and Z together may form a dioxo-substituted pyrrole ring; and the corresponding non-toxic pharmaceutically acceptable salts thereof.

An additional particularly preferred group of compounds having the structural formula I above are those wherein $R_1$ represents hydrogen, halogen, lower alkoxy, hydroxy or acetoxy; $R_2$ represents lower alkyl, trifluoromethyl, alkoxycarbonyl, carboxy or lower alkyl carboxylic acid; and Z represents cyano, carboxy, alkoxycarbonyl or $$-\overset{\overset{\displaystyle O}{\|}}{C}-X$$

wherein X represents amino, N-lower-alkylamino, hydroxylamino, N-methylhydroxylamino, ureido, piperidino, or anilino; and wherein $R_2$ and Z together may form a dioxo-substituted pyrrole ring; and the corresponding non-toxic pharmaceutically acceptable salts thereof.

The compounds of this invention are active in the prevention of allergic and asthmatic conditions. For example, in tests conducted by the procedures described in Mota, I., *Life Sciences*, 7: 465 (1963) and Ovary, Z. et al., *Proc. Soc. Exptl. Biol. Med.*, 81: 584 (1952), these compounds are capable of protecting mammals such as rats and guinea pigs from allergic and asthmatic conditions at dose levels of from 5 to 100 mg/kg, when administered parenterally or orally. In use, the compounds of this invention may be combined with a parenterally acceptable vehicle such as a gum tragacanth saline suspension to provide dosage forms suitable for parenteral administration; or they may be combined with pharmaceutical diluents such as lactose, cornstarch, microcrystalline cellulose, Polyethylene Glycol 4000 and/or 6000, and the like, and formulated into tablet or capsule forms. A dose of 5 to 100 mg/kg of body weight is suggested for relieving allergic conditions. This dosage regimen may be varied depending upon the severity of the condition, the age, weight, and sex of the mammal being treated and the route of administration.

For treating human beings, a dose of 50 to 100 mg administered four times daily, orally or by inhalation in the form of an aerosal spray, is prescribed to give symptomatic relief of asthma. The therapeutic spectrum of the compounds of this invention may be broadened by combination with sympathomimetic agents such as isoproterenol or with steroids such as cortisone or its derivatives orally or by inhalation in the form of an aerosal spray, is prescribed to give symptomatic relief of asthma. The therapeutic spectrum of the compounds of this invention may be broadened by combination with sympathomimetic agents such as isoproterenol or with steroids such as cortisone or its derivatives.

In addition to the above pharmaceutical activities, certain compounds of this invention also exhibit anti-secretory effects and gastric anti-ulcer activity in experimental mammals such as rats. Compounds demonstrating this last mentioned activity include those compounds of the general formula I above wherein $R_1$ represents hydrogen, halogen, lower alkoxy, hydroxy, or acetoxy; $R_2$ represents hydrogen, lower alkyl, trifluoromethyl, alkoxycarbonyl; carboxy or lower alkyl carboxylic acid; and Z represents cyano. When these 3-cyano derivatives are tested according to the procedure described in Shay, H. et al., *Gastroenterology* 5: 43 (1945), in the pylorus ligated rat, they exhibit an $ED_{50}$ of 20 mg to 50 mg/kg of body weight.

The compounds of this invention may be prepared by a number of different procedures. For example, compounds of the general formula IV:

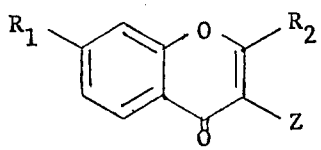

IV wherein $R_1$ represents hydroxy, lower alkoxy, or acyloxy; $R_2$ represents hydrogen, lower alkyl, fluorinated lower alkyl, alkoxycarbonyl, carboxy or lower carboxylic acid; and Z represents cyano, carbamoyl or carboxy; and $R_2$ and Z may together form a substituted pyrrole ring, are prepared by a novel process described in U.S. Pat. No. 3,825,574 starting with substituted o-hydroxybenzoyl acetonitriles. The starting substituted orthohydroxybenzoyl acetonitriles, having the structure V:

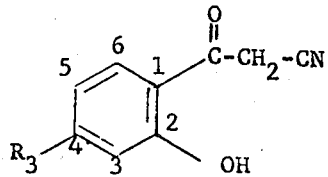

V wherein $R_3$ is hydroxy or lower alkoxy are easily prepared by known methods or obvious adaptations thereof, as described in Chem. Ber. 50: 1292–1305 (1917).

According to the novel process described in aforementioned U.S. Pat. No. 3,825,574, o-hydroxy-benzoyl acetonitriles having the general formula V above are reacted with an acid derivative having the formula VI, VII, or VIII:

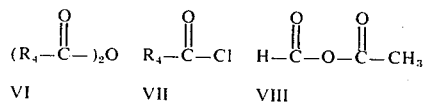

VI  VII  VIII wherein $R_4$ represents lower alkyl, fluorinated lower alkyl, carbalkoxy, or, together with the

of formula VI, forms an up to 5 carbon atom cyclic anhydride, in the presence of a base such as triethylamine, an alkali metal hydride, alkoxide, or hydroxide, or preferably, pyridine. Acylation and subsequent ring closure take place to afford a chromone nitrile of formula IX wherein $R_1$ and $R_2$ have the meanings described above for formula IV:

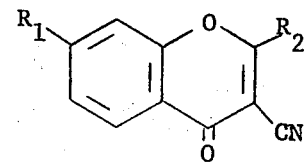

IX

One of the especially preferred features of this novel process is the facility with which chromone derivatives having substituents in the 2-position are prepared, i.e., through the use of the acid reactant VI or VII above. Suitable acid reactants include acetic anhydride, acetylchloride, succinic anhydride, trifluroacetic anhydride or ethyl oxalyl chloride.

In order to prepare compounds according to structure IX in which $R_2$ represents hydrogen, the acid derivative used is the aceticformic anhydride of formula VIII above. The phenolic oxygen in position 7 is also acylated under these conditions and may be isolated as such, or the acyl group may be hydrolyzed during workup. In the former case, treatment with a mild base regenerates the phenol.

In the second step of the novel process of this invention, compounds having the formula IX above are hydrolyzed to the corresponding amides or acids with mineral acid. Acids which may be used are hydrochloric, sulfuric, phosphoric and the like.

In the case where $R_2$ represents ethoxycarbonyl and Z represents carbamoyl, further refluxing with acid promotes ring closure and the formation of a substituted-pyrrole ring, i.e. a dioxo-substituted pyrrole ring.

Similarly, compounds of the instant invention having the general formula X:

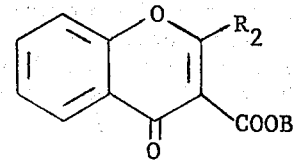

X wherein $R_2$ and B equal lower alkyl, are prepared using a compound of the formula XI:

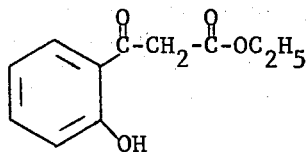

XI as a starting material. Compound XI which is described in Casini, G. et al., *J. Het. Chem.* 6: 279 (1969), is reacted with acetic anhydride and a base, such as potassium carbonate, to afford a 2-substituted-chromone- 3-carboxylic acid ester having formula X, which may be converted to the corresponding 3-carboxylic acid by reaction with aqueous hydrochloric acid.

Other compounds of the instant invention, having the general formula XII:

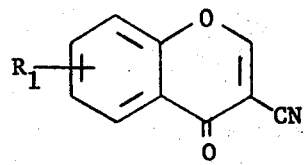

wherein $R_1$ represents hydrogen, halogen, or lower alkoxy, are prepared by a novel process described in U.S. Pat. No. 3,853,921. As described in aforementioned U.S. Pat. No. 3,853,921, compound XII is prepared by refluxing together a 3-formylchromone having formula XIII:

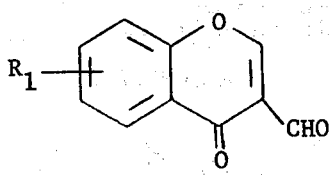

with formic acid and hydroxylamine. Starting Compound XIII is prepared by oxidizing 3-(hydroxymethyl)chromones with an oxidizing agent, such as sodium dichromate with glacial acetic acid, concentrated nitric acid or potassium persulfate. The 3-(hydroxymethyl)chromones are prepared in accordance with the description set forth in U.S. Pat. Ser. No. 3,798,240.

Additional compounds of the instant invention, having the general formula XIV:

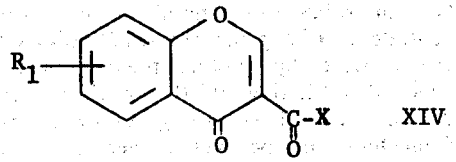

wherein $R_1$ represents hydrogen, halogen, or lower alkyl and X represents amino, N-lower-alkylamino, hydroxylamino, N-lower-alkylhydroxylamino, ureido, piperidino, or anilino are prepared by treating an acid chloride of the formula XV:

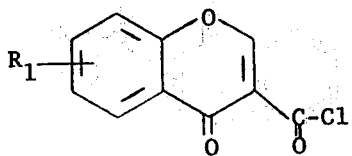

wherein $R_1$ is as described in formula XIV above, with the appropriate amines, hydroxylamines, ammonium hydroxide, piperidines, anilines, urea or hydrozines employing standard procedures. The starting acid chloride XV is prepared in accordance with the procedure set forth in U.S. Pat. No. 3,849,446.

Salts of acidic compounds of this invention may be prepared using known techniques, i.e., by combination with an equivalent amount of an inorganic base; by combination with an alkali metal salt of a lower alkyl carboxylic acid; or by combination with an equivalent amount of an organic base in an appropriate solvent.

In all of the above formulas, definitions for $R_1$, $R_2$, $R_3$, $R_4$, Z, X, and B are based on the following meanings: the term "lower alkyl" and the alkyl portion of "lower alkoxy" are meant to include lower aliphatic hydrocarbons having from 1 to 7 carbon atoms in the carbon chain, preferably 1 to 4 carbon atoms, such as methyl, ethyl, propyl, isopropyl, butyl, or isobutyl.

The term "acyloxy" is meant to include lower alkyl carboxylic acids wherein "lower alkyl" has the above described meaning. Similarly in the term "alkoxycarbonyl" the alkoxy moiety is meant to include lower aliphatic hydrocarbon groups of 1 to 7 carbon atoms, preferably 1 to 4 carbon atoms, as described above.

The term "lower carboxylic acid" is meant to include carboxylic acids in which the aliphatic hydrocarbon chain contains from 1 to 4 carbon atoms.

The term "fluorinated lower alkyl" is meant to include lower alkyl groups as described above wherein one or more hydrogen atoms have been replaced by fluorine.

The following examples are provided to further illustrate our invention.

EXAMPLE 1

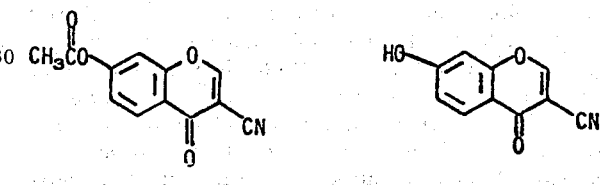

7-Hydroxy-4-oxo-4H-1-benzopyran-3-carbonitrile acetate and
7-Hydroxy-4-oxo-4H-1-benzopyran-3-carbonitrile.

To a mixture of 105 g (1.2 mol) of formyl acetic anhydride and 40 ml of pyridine cooled to −10°C was added 16.5 g (0.1 mol) of 2,4-dihydroxybenzoylacetonitrile. This mixture was stirred overnight, allowing the reaction to warm to room temperature. The mixture was evaporated in vacuo and the residue was triturated with ethanol and filtered to give 23.3 g of crude material. Recrystallization of this solid from absolute ethanol gave 5.3 g of 7-hydroxy-4-oxo-4H-1-benzopyran-3-carbonitrile acetate, mp 178°–180°C.

Anal. Calcd. $C_{12}H_7O_4N$: C, 62.89; H, 3.08, N, 6.11. Found: C, 63.18; H, 3.25; N, 6.22.

The ethanolic filtrate from the recrystallization was evaporated and the residue was dissolved in dil. ammonium hydroxide soln. This was then acidified with 2N hydrochloric acid to give 7-hydroxy-4-oxo-4H-1-benzopyran-3-carbonitrile, mp 292°–293°C.

Anal. Calcd. for $C_{10}H_5O_3N$: C, 64.17; H, 2.69; N, 7.48. Found: C, 64.19; H, 2.86; N, 7.46.

EXAMPLE 2

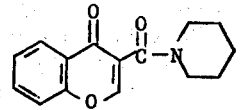

1-[(4-oxo-4H-1-benzopyran-3-yl)carbonyl]piperidine.

A solution of 6.0 g (0.029 mol) of chromone-3-carbonylchloride was added over several minutes to a stirred solution of 15.6 g (0.18 mol) of piperidine in 120 ml of chloroform. The temperature rose to 50°. After 5 minutes the solution was poured into a mixture of 200 ml 1N hydrochloric acid and 200 g of ice. The organic phase was separated, dried ($Na_2SO_4$) filtered and concentrated; wt 4.8 g (64%); mp 127°–130°. Recrystallization from ethylacetate gave pure amide; mp 133°–135°.

Anal. Calcd. for $C_{15}H_{15}NO_3$: C, 70.02; H, 5.88; N, 5.44. Found: C, 69.75; H, 5.72; N, 5.35.

EXAMPLE 3

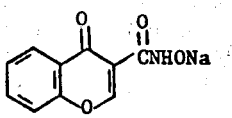

Sodium 4-oxo-4H-1-benzopyran-3-carbohydroxamate.

A solution of 8.34 g (0.12 mol) of hydroxylamine hydrochloride in 125 ml of water was mixed with 100 ml of methylenechloride. Solid sodium carbonate (50 g) was added with cooling. With stirring, a solution of 16.5 g (0.079 mol) of chromone-3-carbonylchloride in 250 ml of methylene chloride was added over a period of 5 minutes, keeping the temp. at 15° with ice bath cooling. After 15 minutes reaction time the thick mixture was filtered and washed with 200 ml of ice-water. The damp filter cake was recrystallized from 100 ml of water, wt 1.5 g (8.4%); mp > 300°.

Anal. Calcd. for $C_{10}H_7NO_4Na$: C, 52.88; H, 2.66; N, 6.17; Na, 10.12. Found: C, 53.12; H, 2.78; N, 6.22; Na, 10.01.

EXAMPLE 4

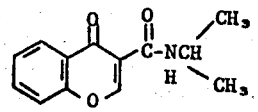

N-isopropyl-4-oxo-4H-1-benzopyran-3-carboxamide.

A solution of 10.4 g (0.05 mol) of chromone-3-carbonylchloride in 200 ml of methylenechloride was added over a 5 minute period to a stirred mixture of 4.13 g (0.07 mol) of isopropylamine, 200 ml of methylenechloride and 25 g of potassium carbonate powder, keeping the temperature at 20° with ice bath cooling. After 15 minutes the solids were filtered and 300 ml of ether was added to the filtrate. This solution was washed twice with 100 ml of water and then twice with 100 ml of 2% sodium bicarbonate (to remove the chromone-3-carboxylic acid impurity). The organic phase was dried ($Na_2SO_4$), filtered and concentrated to give 7.5 g (65%) of crude product; mp 104°–106°. Recrystallization from ether gave pure amide; mp 106°–108°.

Anal. Calcd. for $C_{13}H_{13}NO_3$: C, 67.52; H, 5.67; N, 6.06. Found: C, 67.29; H, 5.62; N, 6.06.

EXAMPLE 5

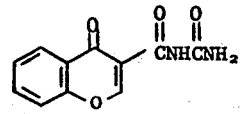

[(4-oxo-4H-1-benzopyran-3-yl)carbonyl]urea.

A hot solution of 10.4 g (0.05 mol) of chromone-3-carbonylchloride in 150 ml of benzene was added over two minutes to a stirred boiling mixture of 3.6 g (0.06 mol) of urea, 100 ml of benzene and two drops of conc. sulfuric acid. The mixture was stirred at reflux for 2 hrs., cooled and filtered; wt 12.3 g; mp 200°–217°. Recrystallization from dimethylformamide gave 63% yield of pure product, mp 247°–250°.

Anal. Calcd. for $C_{11}H_8N_2O_4$: C, 56.90; H, 3.47; N, 12.07. Found: C, 56.85; H, 3.45; N, 12.08.

EXAMPLE 6

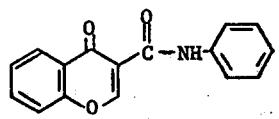

4-oxo-4H-1-benzopyran-3-carboxanilide.

A solution of 10.4 g (0.04 mol) of chromone-3-carbonylchloride in 200 ml of methylenechloride was added over a period of 5 minutes to a stirred mixture of 6.51 g (0.07 mol) of aniline, 30 g powdered potassium carbonate and 100 ml of methylenechloride, keeping the temperature at 25° with ice bath cooling. After one hour the solids were filtered and the filtrate was concentrated; wt 7.5 g; mp 215°–217°. Additional material was recovered by dissolving the carbonate filtercake in water and filtering off the product; wt 4.9 g; mp 215°–217°; total wt 12.4 g (94%). Recrystallization from chloroform-petroleum ether gave pure amide; mp 215°–217°.

Anal. Calcd. for $C_{16}H_{11}NO_3$: C, 72.44; H, 4.18; N, 5.28. Found: C, 72.42; H, 4.27; N, 5.25.

EXAMPLE 7

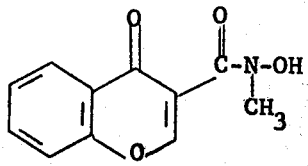

N-methyl-4-oxo-4H-1-benzopyran-3-carbohydroxamic acid.

A quantity of 6.26 g (0.075 mol) of N-methylhydroxylamine hydrochloride (50% excess) was dissolved in 25 ml of water. Chloroform (50 ml) and then excess potassium carbonate was added to saturate the aqueous phase. With stirring a solution of 10.4 g (0.05 mol) of chromone-3-carbonylchloride in 125 ml of chloroform was added. After one hour the solids, containing the potassium salt of the product, were filtered and the filtercake was dissolved in 100 ml of water and acidified with acetic acid to give 6.2 g of the free hydroxamic acid; mp 174°–176°. Another 2.2 g of free hydroxamic acid was obtained from the above chloroform filtrate; mp 178°–181°; total wt 8.4 g (77%). Recrystallization from 2-propanol gave pure product; mp 192°–194°.

Anal. Calcd. for $C_{11}H_9NO_4$: C, 60.27; H, 4.14; N, 6.39. Found: C, 60.21; H, 4.11; N, 6.33.

EXAMPLE 8

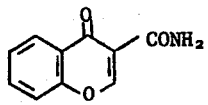

4-oxo-4H-1-benzopyran-3-carboxamide.

A quantity of 0.9 g (0.0043 mol) of 4-oxo-4H-1-benzopyran-3-carbonylchloride was added gradually to a stirred quantity of 15 ml of conc. ammonium hydroxide at room temperature. All solid went into solution when crystals gradually separated. After 15 min. the solid was filtered and washed with water; wt 0.4 g (48.8% yield); mp 220°–225°. Two recrystallizations from 2-propanol gave pure material melting at 250°–252°C.

Anal. Calcd. for $C_{10}H_7NO_3$: C, 63.49; H, 3.73; N, 7.41. Found: C, 63.57; H, 3.83; N, 7.55.

EXAMPLE 9

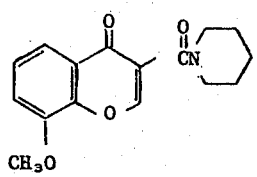

1-[8-methoxy-4-oxo-4H-1-benzopyran-3-yl)carbonyl]-piperidine

A solution of 5.0 g. (0.021 mole) of 8-methoxy-4-oxo-4H-1-benzopyran-3-carbonyl chloride in 100 ml of chloroform was added to a stirred solution of 20 g. of piperidine in 100 ml. of methylene chloride over a period of five minutes. The temperature rose to 35°C. After 15 minutes reaction time the solution was stirred with 350 ml. 1N hydrochloric acid for 15 minutes. The organic phase was separated, dried over $MgSO_4$ and concentrated to give 3.8 g. (63%) of crude solid. Recrystallization from ethylacetate gave pure amide; m.p. 202°–204°.

Anal. Calcd. for $C_{16}H_{17}NO_4$: C, 66.88; H, 5.96; N, 4.88. Found: C, 67.04; H, 5.97; N, 4.82.

EXAMPLE 10

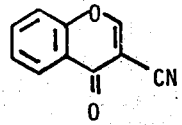

4-Oxo-4H-1-Benzopyran-3-carbonitrile

A mixture of 26.1 g. (0.15 mole) of 4-oxo-4H-1-benzopyran-3-carboxaldehyde, 13.1 g. (0.19 mole) of hydroxylamine hydrochloride, 18.4 g. (0.27 mole) of sodium formate and 250 ml of 99% formic acid was heated with stirring at reflux for 2½ hours. Water was added to 1-liter volume. The separated solid was filtered from the cooled mixture, washed well with water and dried to give 13 g. (51%) of crude nitrile melting at 138°–145°C. Recrystallization from ethylacetate gave pure, white crystals melting at 174°–176°.

Anal. Calcd for $C_{10}H_5NO_2$: C, 70.17; H, 2.94; N, 8.18. Found: C, 70.18; H, 3.05; N, 8.22.

EXAMPLE 11

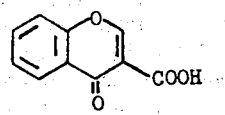

4-Oxo-4H-1-Benzopyran-3-Carboxylic Acid

A mixture of 3.1 g. (0.018 mole) of 4-oxo-4H-1-benzopyran-3-carbonitrile and 100 ml of conc. hydrochloric acid was heated at reflux for one-half hour. All solid went into solution at 15 min. and solid began to separate at the end of one-half hour. The mixture was concentrated at reduced pressure to one-half volume. Water (100 ml) was added to precipitate additional solid. The filtered solid was washed with 20 ml of water and dried to give 2.5 g. of crude acid.

Purification was effected by stirring the above crude acid with 250 ml of 5% sodium bicarbonate, extracting most of the undissolved solid with 50% ether-methylene chloride, separating aqueous phase, acidifying with conc. hydrochloric acid and filtration of separated 3-carboxylic acid product; wt. 1.9 g., m.p. 190°–195°C; % yield = 55.2. Recrystallization from ethylacetate gave pure material melting at 199°–201°C.

Anal. Calcd for $C_{10}H_6O_4$: C, 63.16; H, 3.18. Found: C, 62.93; H, 3.19.

EXAMPLE 12

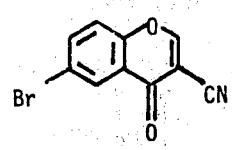

6-Bromo-4-Oxo-4H-1-Benzopyran-3-Carbonitrile

A mixture of 5.06 g. (0.02 mole) of 6-bromo-4-oxo-4H-1-benzopyran-3-carboxaldehyde, 1.53 g. (0.022 mole) of hydroxylamine hydrochloride, 2.72 g. (0.04 mole) of sodium formate and 100 ml of 99% formic acid was heated to reflux. The resulting solution was maintained at reflux for 2½ hours. Water (300 ml) was added to precipitate 3.1 g. of crude nitrile; m.p. 211–215. Recrystallization from acetonitrile-water gave 1.5 g. of purified nitrile (30% yield); m.p 215°–218°. Further recrystallization from acetonitrile gave analytical quality nitrile; m.p. 216°–219°.

Anal. Calcd for $C_{10}H_4NO_2Br$: C, 48.03; H, 1.61; N, 5.60. Found: C, 47.90; H, 1.65; N, 5.54.

EXAMPLE 13

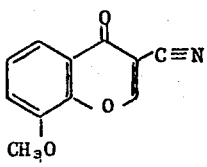

8-Methoxy-4-oxo-4H-1-benzopyran-3-carbonitrile

A mixture of 5.2 g. (0.026 mole) of 8-methoxy-4-oxo-4H-1-benzopyran-3-carboxaldehyde, 2.08 g. (0.03 mole) of hydroxylamine hydrochloride and 75 ml. of 97% formic acid was heated with stirring until all solid dissolved (T=60°C). A quantity of 3.4 g. (0.05 mole) of sodium formate was added. The resulting slurry was heated to reflux. After 15 minutes all solid was in solution. After 3 hours of reflux the solution was cooled, water (300 ml.) was added and the separated solid was filtered, washed with water and dried; wt. 3.6 g. (68%); m.p. 225°–230°. Recrystallization from tetrahydrofuran gave pure nitrile; m.p. 232°–234°.

Anal. Calcd for $C_{11}H_7NO_3$: C, 65.67; H, 3.51; N, 6.96. Found: C, 65.71; H, 3.48; N, 7.05.

EXAMPLE 14

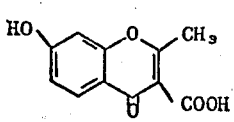

7-Hydroxy-2-methyl-4-oxo-4H-1-benzopyran-3-carboxylic acid.

A mixture of 5.2 g of 7-hydroxy-4-oxo-2-methyl-4H-1-benzopyran-3-carbonitrile, 20 ml of conc. sulfuric acid and 5 ml of water was heated for 5 hours at an internal temperature of 130°. The mixture was poured onto ice. The solid was filtered and recrystallized from ethanol, mp 286°–287°C.

Anal. Calcd. for $C_{11}H_8O_5$: C, 60.00; H, 3.66. Found: C, 59.93; H, 3.55.

EXAMPLE 15

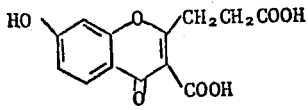

3-Carboxy-7-hydroxy-4-oxo-4H-1-benzopyran-2-propionic acid.

Prepared from 3-cyano-7-hydroxy-4-oxo-4H-1-benzopyran-2-propionic acid as described in Example 14. The product was recrystallized from ethanol, mp 218°–219°C.

Anal. Calcd for $C_{13}H_{10}O_7$: C, 56.12; H, 3.62. Found: C, 55.69; H, 3.70.

EXAMPLE 16

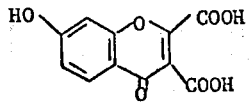

7-Hydroxy-4-oxo-4H-1-benzopyran-2,3-dicarboxylic acid.

A mixture of 2.0 g (7.2 mmol) of ethyl 3-carbamoyl-7-hydroxy-4-oxo-4H-1-benzopyran-2-carboxylate in 10 ml of 80% sulfuric acid was heated over a steam bath for 1 hr. and then poured into 50 ml of water. This was filtered and the filtrate evaporated in vacuo. The gummy residue was triturated with a minimum amount of water, the solid filtered and dried, mp 255°–257°C.

Anal. Calcd. for $C_{11}H_6O_7$: C, 52.81; H, 2.42. Found: C, 52.89; H, 2.87.

EXAMPLE 17

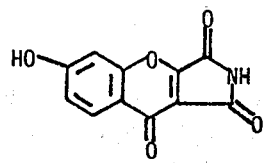

3,4-Dihydro-7-hydroxy-4H-pyrrolo[3,4-b][1]benzopyran-1,3,4(2H)-trione.

A mixture of 3.5 g (0.013 mol) of ethyl 3-carbamoyl-7-hydroxy-4-oxo-4H-1-benzopyran-2-carboxylate in 100 ml of glacial acetic acid was refluxed for 3 hrs. The solid was filtered and recrystallized from aqueous dimethylformamide, mp > 300°C.

Anal. Calcd. for $C_{11}H_5O_5N$: C, 57.15; H, 2.18; N, 6.06. Found: C, 56.89; H, 2.32; N, 5.93.

EXAMPLE 18

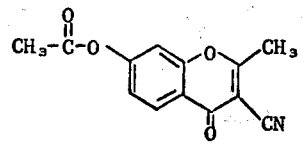

7-Acetoxy-4-oxo-2-methyl-4H-1-benzopyran-3-carbonitrile.

A mixture of 5 g of 2,4-dihydroxybenzoyl acetonitrile, 15 ml of pyridine and 7.5 ml of acetic anhydride was left overnight at room temperature. The next morning the crystals were filtered and recrystallized from ethanol, mp 140°–141° C.

Anal. Calcd. for $C_{13}H_9NO_4$: C, 64.20; H, 3.73, N, 5.76. Found: C, 64.07; H, 3.73; N, 5.76.

EXAMPLE 19

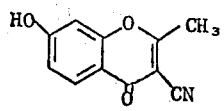

7-Hydroxy-4-oxo-2-methyl-4H-1-benzopyran-3-carbonitrile.

A slurry of 7.3 g of 7-acetoxy-4-oxo-2-methyl-4H-1-benzopyran-3-carbonitrile in 45 ml of methanol was treated with 75 ml of 1N sodium hydroxide solution. The mixture was stirred for 5 minutes, cooled in ice and

EXAMPLE 20

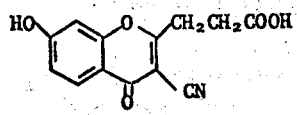

3-Cyano-7-hydroxy-4-oxo-4H-1-benzopyran-2-propionic acid.

A mixture of 8.85 g of 2,4-dihydroxybenzoyl acetonitrile, 25 ml of pyridine and 15 g of succinic anhydride was stirred at room temperature overnight. The next morning the solid was filtered and recrystallized from methanol, mp 300°–301° C.

Anal. Calcd. for $C_{13}H_9NO_5$: C, 60.24; H, 3.50; N, 5.40. Found: C, 59.96; H, 3.46; N, 5.25.

EXAMPLE 21

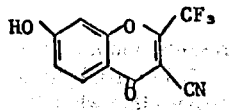

7-Hydroxy-4-oxo-2-(trifluoromethyl)-4H-1-benzopyran-3-carbonitrile.

A slurry of 8.85 g of 2,4-dihydroxybenzoyl acetonitrile in 40 ml of trifluoroacetic anhydride was cooled to 0°C. and treated dropwise with 7 ml of pyridine. The resulting yellow solution was set aside at room temperature for 6 days. The reaction mixture was concentrated to a paste, water and ice were added, and the solid product filtered. Recrystallization from acetonitrile gave the analytical sample, mp 255°–257° C.

Anal. Calcd. for $C_{11}H_4NO_3F_3$: C, 51.78; H, 1.58, N, 5.49. Found: C, 51.82; H, 1.66; N, 5.92.

EXAMPLE 22

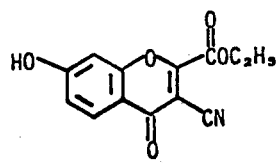

Ethyl 3-cyano-7-hydroxy-4-oxo-4H-1-benzopyran-2-carboxylate.

A mixture of 12.82 g (0.08 mol) of 2,4-dihydroxybenzoylacetonitrile, 32.8 g (0.24 mol) of ethyl oxalyl chloride and 120 ml of pyridine was stirred overnight. The mixture was filtered, the cake was discarded, and the filtrate evaporated in vacuo to give a dark brown oil. This was slowly poured into cold 2NHCl. The solid was filtered and recrystallized from ethanol gave 13.7 g (66%) of cream colored plates, mp 262°–264°C.

Anal. Calcd. for $C_{13}H_9O_5N$: C, 60.24; H, 3.50; N, 5.40. Found: C, 60.48; H, 3.52; N, 5.36.

EXAMPLE 23

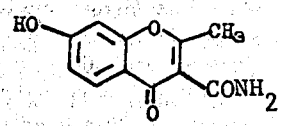

7-Hydroxy-4-oxo-2-methyl-4H-1-benzopyran-3-carboxamide.

A slurry of 1 g of 7-hydroxy-4-oxo-2-methyl-4H-1-benzopyran-3-carbonitrile in 6 ml of conc. sulfuric acid was heated for 3 hours on the steam bath. The mixture was poured onto ice. The solid was filtered and recrystallized from ethanol, mp 289°–290°C.

Anal. Calcd. for $C_{11}H_9NO_4$: C, 60.27; H, 4.14; N, 6.39. Found: C, 60.17; H, 4.12; N, 5.90.

EXAMPLE 24

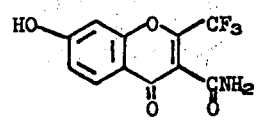

7-Hydroxy-4-oxo-2-(trifluoromethyl)-4H-1-benzopyran-3-carboxamide.

A mixture of 3 g of 7-hydroxy-4-oxo-2-(trifluoromethyl)-4H-1-benzopyran-3-carbonitrile, 4 ml of conc. sulfuric acid and 1 ml of water was heated for 1½ hours at an internal temperature of 120°–135°C. The clear dark solution was poured onto ice. The solid was filtered and recrystallized from methanol, mp > 310° C.

Anal. Calcd. for $C_{11}H_6NO_4F_3$: C, 48.37; H, 2.21; N, 5.13. Found: C, 48.41; H, 2.21; N, 4.99.

EXAMPLE 25

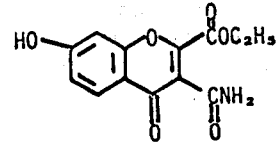

Ethyl 3-carbamoyl-7-hydroxy-4-oxo-4H-1-benzopyran-2-carboxylate.

A mixture of 25.0 g (0.097 mol) of ethyl 3-cyano-7-hydroxy-4-oxo-4H-1-benzopyran-2-carboxylate in 230 ml conc. sulfuric acid was stirred at room temperature overnight. The mixture was then poured into 1.5 l of ice water with stirring. The resulting solid was filtered off, washed with water, and dried. 16.5 g (60%) mp > 320° C. from acetonitrile.

Anal. Calcd. for $C_{13}H_{11}O_6N$: C, 56.32; H, 4.00; N, 5.05. Found: C, 56.20; H, 4.08; N, 5.32.

EXAMPLE 26

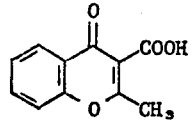

2-Methyl-4-oxo-4H-1-benzopyran-3-carboxylic acid.

A solution of 10.0 g. (0.0458 mole) of methyl 2-methyl-4-oxo-4H-1-benzopyran-3-carboxylate in 100 ml. of conc. hydrochloric acid was maintained at 80°–90° for 20 minutes. Ice (400 g.) was added and the separated tacky solid was filtered and washed well with water. The crude product was dissolved in 300 ml. of 5% sodium bicarbonate and the insoluble portion was extracted away with 300 ml. of ether. The aqueous phase was acidified with conc. hydrochloric acid to give 6.4 g. (68.3%) of white acid; m.p. 120°–135°. Recrystallization from 2-propanol gave pure product; m.p. 145°–147°.

Anal. Calcd for $C_{11}H_8O_4$: C, 64.70; H, 3.95. Found: C, 64.79; H, 4.11.

EXAMPLE 27

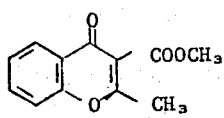

Methyl 2-methyl-4-oxo-4H-1-benzopyran-3-carboxylate.

A stirred mixture of 22.0 g. (0.112 mole) of methyl salicyloylacetate, 600 ml. of xylene, 60 g. of powdered potassium carbonate and 60 ml. of acetic anhydride was heated to 80°. After evolution of $CO_2$ was complete the temperature was raised to 125°–130° for one hour. The mixture was filtered and the filtrate stirred for 2 hours with 200 ml. of water. The organic phase was separated, washed twice with 100 ml. of water, dried over $Na_2SO_4$ and concentrated to give 15 g. (61.5%) of tacky ester. Recrystallization from ethylacetate gave pure product; m.p. 116°–118°.

Anal. Calcd for $C_{12}H_{10}O_4$: C, 66.05; H, 4.62. Found: C, 66.03; H, 4.59.

We claim:
1. A method for preventing asthmatic symptoms in a mammal in need thereof which comprises the administration of from about 5 to about 100 mg/kg of body weight of a compound of the formula:

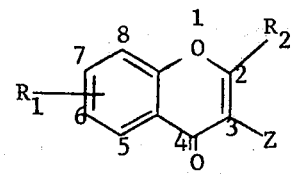

wherein $R_1$ represents hydrogen, halogen, lower alkyl, hydroxy, lower alkoxy, or lower alkanoyloxy; $R_2$ represents hydrogen, lower alkyl, fluorinated lower alkyl, lower alkoxycarbonyl, carboxy, or lower alkyl carboxylic acid; Z represents cyano, carboxy, lower alkoxycarbonyl or

wherein X represents amino, N-lower-alkyl-amino, hydroxylamino, N-lower-alkylhydroxylamino, or ureido, with the proviso that when $R_2$ represents hydrogen, Z represents cyano or

wherein X has the same meaning as given above; or the corresponding non-toxic, pharmaceutically acceptable salts thereof.

* * * * *